(12) United States Patent
Ikeda et al.

(10) Patent No.: US 8,978,490 B2
(45) Date of Patent: Mar. 17, 2015

(54) INERTIAL FILTER AND PARTICLE CLASSIFICATION APPARATUS

(75) Inventors: Takuji Ikeda, Nara (JP); Yoshio Otani, Ishikawa (JP); Masami Furuuchi, Ishikawa (JP); Takafumi Seto, Ishikawa (JP); Masato Mizuno, Tokyo (JP)

(73) Assignee: Nitta Corporation, Osaka (JP)

(*) Notice: Subject to any disclaimer, the term of this patent is extended or adjusted under 35 U.S.C. 154(b) by 155 days.

(21) Appl. No.: 13/806,118

(22) PCT Filed: Nov. 2, 2010

(86) PCT No.: PCT/JP2010/006458
§ 371 (c)(1),
(2), (4) Date: Dec. 20, 2012

(87) PCT Pub. No.: WO2012/001752
PCT Pub. Date: Jan. 5, 2012

(65) Prior Publication Data
US 2013/0086876 A1 Apr. 11, 2013

(30) Foreign Application Priority Data

Jun. 30, 2010 (JP) ................. 2010-148870

(51) Int. Cl.
*B01D 45/04* (2006.01)
*G01N 1/22* (2006.01)
*G01N 15/02* (2006.01)

(52) U.S. Cl.
CPC .............. *B01D 45/04* (2013.01); *G01N 1/2205* (2013.01); *G01N 15/0255* (2013.01); *G01N 15/0272* (2013.01)
USPC ...................................... 73/863.23; 73/28.04

(58) Field of Classification Search
CPC .... B01D 45/04; B01D 45/08; G01N 15/0255; G01N 15/0272; G01N 1/2205
USPC ........ 73/28.04, 28.05, 28.06, 863.22, 863.23; 55/418, 465
See application file for complete search history.

(56) References Cited

U.S. PATENT DOCUMENTS

| 4,606,232 A | 8/1986 | Prodl |
| 2006/0248632 A1 | 11/2006 | Colombo |

FOREIGN PATENT DOCUMENTS

| JP | 60-015542 A | 1/1985 |
| JP | 61-291014 A | 12/1986 |
| JP | 61-21768 A | 5/1994 |
| JP | 2001-104736 A | 4/2001 |
| JP | 2002-035698 A | 2/2002 |
| JP | 2006-198577 A | 8/2006 |
| JP | 2006-263713 A | 10/2006 |
| JP | 2007-501339 A | 1/2007 |
| JP | 2008-070222 A | 3/2008 |

OTHER PUBLICATIONS

International Search Report mailed Dec. 7, 2010 issued in corresponding International Application No. PCT/JP2010/006458.

*Primary Examiner* — Robert Clemente
(74) *Attorney, Agent, or Firm* — McDermott Will & Emery LLP

(57) ABSTRACT

An inertial filter is placed in a fluid flow path and equipped with a particle classifying sheet having a plurality of particle classifying holes uniformly arranged. The particle classifying sheet has a sheet area larger than a fluid passage area at a site where the sheet is placed. A part of the sheet is provided in the form of a partition wall dividing the fluid flow path in two sections in a fluid passage direction to allow for classification of particles.

18 Claims, 18 Drawing Sheets

|  | diffusion filter | inertial filter |
|---|---|---|
| aimed collecting mechanism | diffusion | inertia |
| wire diameter d (μm) | approximately 20 | 5~20 |
| Aperture D (μm) | approximately 20 | 40~300 |
| filtering speed (m/s) | 0.001~0.1 | 1~100 |

F I G. 1 4
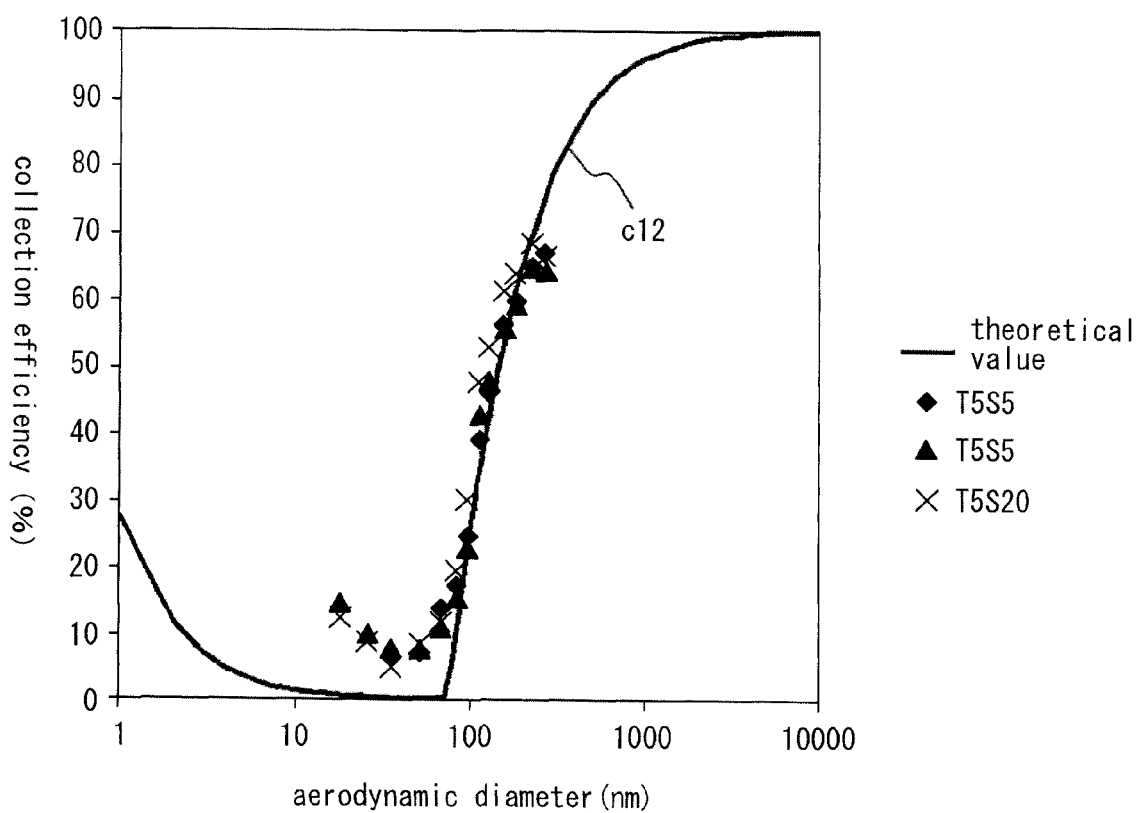

PRIOR ART

INERTIAL FILTER AND PARTICLE CLASSIFICATION APPARATUS

RELATED APPLICATIONS

This application is the U.S. National Phase under 35 U.S.C. §371 of International Application No. PCT/JP2010/006458, filed on Nov. 2, 2010, which in turn claims the benefit of Japanese Application No. 2010-148870, filed on Jun. 30, 2010, the disclosures of which Applications are incorporated by reference herein.

TECHNICAL FIELD

The invention relates to an inertial filter placed in a fluid flow path to classify particles contained in fluid by an effect of inertial impaction and others, and a particle classification apparatus equipped with the inertial filter.

BACKGROUND ART

A conventional inertial filter 100 is described below referring to FIG. 16. The conventional inertial filter 100 is placed in a fluid flow path to classify particles. The conventional filter 100 has a cylindrical filter body 101, and the filter body 101 has a through cavity 102 having a circular shape in cross section and penetrating through from an upstream side to a downstream side in a fluid passage direction. The through cavity 102 includes a diametrically-reduced through cavity 102a provided on the upstream side and having an inner diameter gradually smaller, and a diametrically-constant through cavity 102b continuous to the diametrically-reduced through cavity 102a on the downstream side and having an inner diameter dimensionally fixed. The diametrically-constant through cavity 102b is filled with a metal fiber 103 which is an example of incompressible fibers. The metal fiber 103 is secured by a mechanism not illustrated in the drawing so that the metal fiber 103 does not fall off from the diametrically-constant through cavity 102b and drop downward in the fluid passage direction.

According to the inertial filter 100, an internal pressure of the inertial filter 100 is lowered to or under an external pressure by a suctioning force of a pump not illustrated in the drawing so that a fluid flows in the through cavity 102 from the direction of arrow A to the direction of arrow B by a pressure difference resulting from the internal and external pressures to allow for classification of particles. The fluid increases its velocity of fluid flow in the diametrically-reduced through cavity 102a, and the velocity of fluid flow becomes constant once the fluid enters the diametrically-constant through cavity 102b. Then, fine particles contained in the fluid collide with and captured (collected) by the metal fiber 103 in the diametrically-constant through cavity 102b.

PRIOR ART DOCUMENT

Patent Reference

Patent Reference 1: JP Patent Application Publication No. 2008-70222

SUMMARY OF THE INVENTION

Problem to be Solved by the Invention

The conventional inertial filter 100 has the following technical problems. The first problem is difficulty in achieving aimed initial classifying characteristics because of the lack of uniformity in the spatial density distribution, orientation, and shape of the fiber. The second problem is difficulty in filling the diametrically-constant through cavity 102b with the metal fiber 103 at an equal density. As a result of the random density of the metal fiber 103 filling the diametrically-constant through cavity 102b, the classifying characteristics are easily variable, making it difficult to classify particles in a stable manner. The third problem is the occurrence of compression of the metal fiber 103 in the fluid passage direction under pressure applied by gas flow during the classifying operation. This adversely affects the classifying characteristics, undermining the stability of the classifying operation. The fourth problem is changes possibly occurring during wash of the inertial filter in the spatial density of the metal fiber 103 in the diametrically-constant through cavity 102b because it is difficult to quantity such changes, often compromising reuse of the inertial filter.

Faced with these technical problems, the invention provides an inertial filter wherein an aimed initial classifying performance is easily achievable, and a good collection efficiency is unlikely to deteriorate over a long period of time, thereby enabling to reliably classify particles.

Means for Solving the Problem

1) An inertial filter according to the invention is an inertial filter placed in a fluid flow path and including a particle classifying sheet having a plurality of particle classifying holes uniformly arranged, wherein the particle classifying sheet has a sheet area larger than a fluid passage area at a site where the sheet is placed, and a part of the sheet is provided in the form of a partition wall dividing the fluid flow path in two sections in a fluid passage direction to allow for classification of particles.

Preferably, a sheet constitutes the particle classifying sheet in the fluid passage direction.

Preferably, a plurality of laminated sheets constitutes the particle classifying sheet in the fluid passage direction.

Preferably, the particle classifying sheet is a sheet having a large number of through holes formed in a mesh-like pattern as the plurality of particle classifying holes.

Preferably, the particle classifying sheet is a mesh-like sheet having a wire diameter ranging from 5 to 20 µm and an aperture ranging from 40 to 300 µm.

Preferably, a flow quantity adjusting nozzle located on an upstream side of the particle classifying sheet in the fluid passage direction and having a diametrically-reduced through cavity diametrically smaller in the fluid passage direction is provided in a manner that the flow quantity adjusting nozzle is replaceable with another flow quantity adjusting nozzle having a diametrically-reduced through cavity diametrically reduced by a different diameter reducing ratio to allow for adjustment of a velocity of fluid flow.

Preferably, a flow quantity adjusting nozzle located on an upstream side of the particle classifying sheet in the fluid passage direction and having a diametrically-reduced through cavity diametrically smaller in the fluid passage direction is provided in a manner that the flow quantity adjusting nozzle is replaceable with another flow quantity adjusting nozzle having a different number of the diametrically-reduced through cavities to allow for adjustment of a quantity of fluid flow.

Preferably, a flow quantity adjusting nozzle having a flow path diametrically smaller in the fluid passage direction is provided on an upstream side of the particle classifying sheet in the fluid passage direction, and a plurality of the particle classifying sheets are stacked on each other with an intermediary spacer interposed therebetween.

Preferably, the intermediary spacer is replaceable with another intermediary spacer having a different flow path to allow for adjustment of the velocity of fluid flow.

Preferably, the classification of particles is controllable by changing number of the intermediary spacers stacked in layers.

Preferably, the flow quantity adjusting nozzle is replaceable with another flow quantity adjusting nozzle having a different flow path to allow for adjustment of the velocity of fluid flow.

Preferably, the classification of particles is controllable by changing a spacer thickness dimension of the intermediary spacer.

Preferably, number of flow paths of the flow quantity adjusting nozzle and number of through holes of the intermediary spacer are changed to allow for adjustment of the quantity of fluid flow.

2) A particle classification apparatus according to the invention is equipped with an inertial filter filled with an incompressible fiber on an upstream side in a fluid passage direction for removal of coarse particles and the inertial filter recited in 1) on a downstream side in the fluid passage direction for classification of nano-sized particles.

The fluid is not necessarily limited to gases. The fluid includes liquids and materials of other forms.

The particles captured or collected by the inertial filter are not necessarily limited to particles floating in gases. The particles include particles floating in solvents such as a liquids and materials of other forms. The particles to be classified are not particularly limited. Examples of the particles to be classified are resin-made fine particles, inorganic fine particles, metallic fine particles, and ceramic fine particles. The particles may have any arbitrary shapes.

The incompressible fiber preferably includes a metal fiber. Though a preferable example of the metal fiber is a stainless fiber, the metal fiber is not necessarily limited to the stainless fiber. The metal fiber may be at least a metal fiber selected from aluminum fiber, copper fiber and any other metal fibers. Further, the incompressible fiber may be selected from fibers other than the metal fibers as far as the selected fiber is incompressible and hardly volumetrically changed by fast gas flow passing therethrough.

Effect of the Invention

The invention can provide an inertial filter achieving advantageous initial classifying characteristics, thereby succeeding in classifying particles in a reliable manner over a long period of time.

BRIEF DESCRIPTION OF THE DRAWINGS

FIG. 2A-1 is an enlarged sectional view of a main part illustrating a first shape example (plane weave) of a nano-sized particle classifying sheet provided in the inertial filter according to the preferred embodiment.

FIG. 2A-2 is an enlarged planar view of the main part illustrating the first shape example (plane weave) of the nano-sized particle classifying sheet provided in the inertial filter according to the preferred embodiment.

FIG. 2B-1 is an enlarged sectional view of a main part illustrating a second shape example (twill weave) of the nano-sized particle classifying sheet provided in the inertial filter according to the preferred embodiment.

FIG. 2B-2 is an enlarged planar view of the main part illustrating the second shape example (twill weave) of the nano-sized particle classifying sheet provided in the inertial filter according to the preferred embodiment.

FIG. 6A-1 is a sectional view of a first inertial filter for classification of nano-sized particles used in the particle classification apparatus of FIG. 1.

FIG. 6A-2 is a top view of the first inertial filter for classification of nano-sized particles.

FIG. 6A-3 is a back view of the first inertial filter for classification of nano-sized particles.

FIG. 6B-1 is a sectional view of a second inertial filter for classification of nano-sized particles used in the particle classification apparatus of FIG. 1.

FIG. 6B-2 is a top view of the second inertial filter for classification of nano-sized particles.

FIG. 6B-3 is back view of the second inertial filter for classification of nano-sized particles.

FIG. 13A-1 is a sectional view of an inertial filter (1) when a flow quantity adjusting nozzle and a plurality of intermediary spacers having different shapes and numbers of through holes are combined in the particle classification apparatus where the inertial filter of FIG. 7 is used.

FIG. 13A-2 is an illustration of a shape of the flow quantity adjusting nozzle provided in the inertial filter (1) of FIG. 13A-1, wherein the drawing on left is a top view and the drawing on right is a back view.

FIG. 13A-3 is a planar view of the intermediary spacers provided in the inertial filter (1) of FIG. 13A-1.

FIG. 13B-1 is a sectional view of an inertial filter (2) when a flow quantity adjusting nozzle and a plurality of intermediary spacers having different shapes and numbers of through holes are combined in the particle classification apparatus where the inertial filter of FIG. 7 is used.

FIG. 13B-2 is an illustration of a shape of the flow quantity adjusting nozzle provided in the inertial filter (2) of FIG. 13B-1, wherein the drawing on left is a top view, and the drawing on right is a back view.

FIG. 13B-3 is a planar view of the intermediary spacers provided in the inertial filter (2) of FIG. 13B-1.

FIG. 14 is a graphical illustration for verifying a filtering performance of the inertial filter according to the preferred embodiment, where a lateral axis represents an aerodynamic diameter and a vertical axis represents a collection efficiency.

PREFERRED EMBODIMENT FOR CARRYING OUT THE INVENTION

Figure 1:
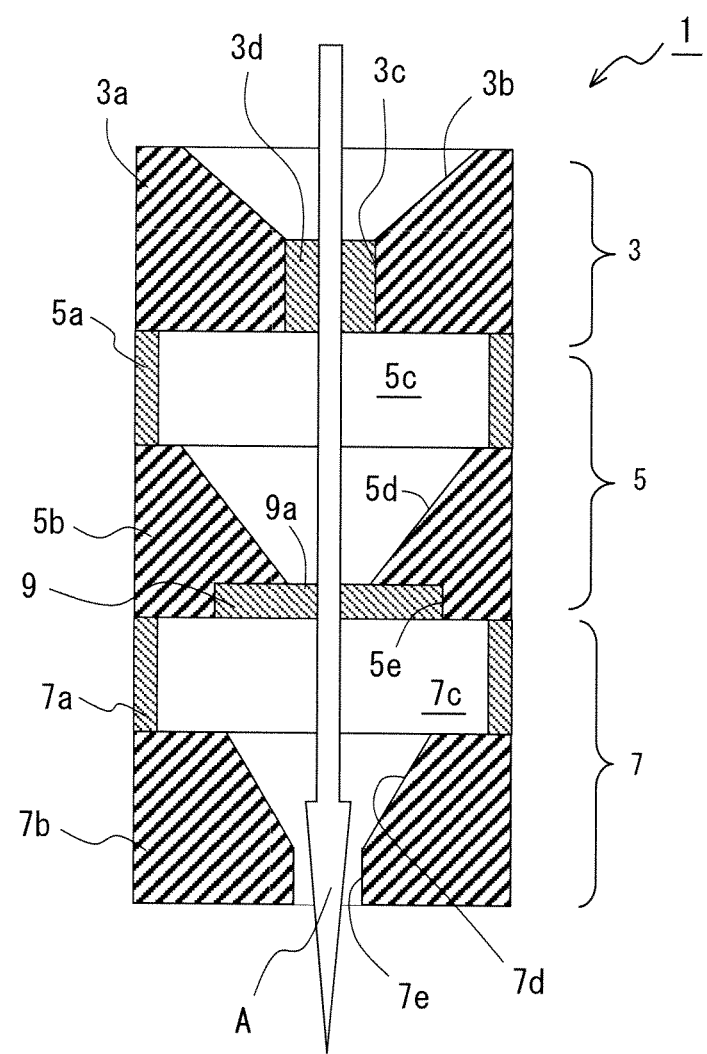
FIG. 1 is an illustration of a particle classification apparatus equipped with an inertial filter according to a preferred embodiment of the invention when viewed from a side surface thereof.

Hereinafter, an inertial filter and a particle classification apparatus equipped with the inertial filter according to a preferred embodiment of the invention are described in detail referring to the accompanied drawings. FIG. 1 is a sectional view of the particle classification apparatus. According to the preferred embodiment, a fluid to be classified containing therein floating particles may be gases, liquids, and solvents of other forms. Describing structural elements of a particle classification apparatus 1 illustrated in FIG. 1 from an upstream side to a downstream side in a fluid passage direction illustrated with arrow A, an inertial filter 3 for removal of coarse particles as a pre-filtering inertial filter, an inertial filter 5 for classification of nano-sized particles as a normal inertial filter, and a nano-sized particle collector/apparatus introduction unit 7.

The inertial filter 3 for removal of coarse particles has a cylindrical plate 3a. The cylindrical plate 3a has a diametrically-reduced through cavity 3b having an inner diameter gradually smaller in the fluid passage direction to expedite a velocity of fluid flow in the fluid passage direction, and a diametrically-constant through cavity 3c continuous to a downstream-side opening of the diametrically-reduced through cavity 3b and having an inner diameter dimensionally fixed in the fluid passage direction to maintain a constant velocity of fluid flow. The diametrically-constant through cavity 3c of the inertial filter 3 for removal of coarse particles is filled with an incompressible fiber densely entangled therein, for example, a metal or preferably SUS (stainless steel) fiber 3d which is hardly volumetrically changed by fast gas flow passing therethrough. In place of the SUS fiber, the metal fiber may be at least a metal fiber selected from aluminum fiber, copper fiber, and other metal fibers. However, the fill-in fiber is not necessarily limited to any of these metal fibers as far as the fiber is incompressible and hardly volumetrically changed by fast gas flow passing therethrough.

The inertial filter 5 for classification of nano-sized particles is continuous to the inertial filter 3 for removal of coarse particles immediately therebelow on the downstream side and coupled with the inertial filter 3 for removal of coarse particles. The inertial filter 5 for classification of nano-sized particle has a cylindrical plate 5a located on the upstream side and structurally characterized in that an outer diameter thereof is equal to an outer diameter of the inertial filter 3 for removal of coarse particles and an inner diameter thereof is dimensionally fixed, and a cylindrical plate 5b having an outer diameter equal to the outer diameter of the cylindrical plate 5a and continuous to the cylindrical plate 5a on the downstream side. These plates constitute a filtering space 5c inside. The cylindrical plate 5b has a diametrically-reduced through cavity 5d formed at a center position thereof and having an inner diameter gradually smaller from the upstream side to the downstream side in the fluid passage direction. A diametrically-constant through cavity 5e having a diametrically fixed inner diameter larger than an inner diameter of a downstream-side opening of the diametrically-reduced through cavity 5d is formed at a lower end of the diametrically-reduced through cavity 5d. A particle classifying sheet 9 is provided at the diametrically-constant through cavity 5e.

The particle classifying sheet 9 has a large number of holes uniformly arranged for classification of nano-sized particles not illustrated in FIG. 1. An example of the particle classifying sheet 9 is a mesh-like sheet. The particle classifying sheet 9 has a sheet area larger than a fluid passage area at a site where the sheet is placed, which is the inner diameter of the downstream-side opening of the diametrically-reduced through cavity 5d in the illustrated example. A part 9a of the sheet is provided in the form of a partition wall dividing a fluid flow path illustrated with arrow A in two sections in the fluid passage direction for classification of particles.

The nano-sized particle collector/apparatus introduction unit 7 has a cylindrical plate 7a located on the upstream side and structurally characterized in that an outer diameter thereof is equal to an outer diameter of the inertial filter 5 for classification of nano-sized particles and an inner diameter thereof is dimensionally fixed, and a cylindrical plate 7b having an outer diameter equal to the outer diameter of the cylindrical plate 7a and continuous to the cylindrical plate 7a on the downstream side. These plates constitute a collecting space 7c inside. The cylindrical plate 7b has a diametrically-reduced through cavity 7d formed at a center position thereof and having an inner diameter gradually smaller from the upstream side to the downstream side in the fluid passage direction, and a diametrically-constant through cavity 7e continuous to the diametrically-reduced through cavity 7d and having a dimensionally fixed inner diameter, thereby guiding the collected nano-sized particles into the apparatus. The apparatus suctions the fluid using a suctioning pump not illustrated in the drawing in the direction illustrated with arrow A to discharge the fluid.

The particle classification apparatus 1 according to the present preferred embodiment described so far is characterized in that the particle classifying sheet 9 having a large number of minute through holes is used in the inertial filter 5 for classification of nano-sized particles in place of filling the diametrically-constant through cavity with any incompressible fiber as described in the conventional structure.

The structural characteristics of the particle classifying sheet 9 are described below referring to FIGS. 2 to 4B. A large number of minute through holes are formed in a mesh-like pattern in the particle classifying sheet 9. Examples of the mesh-like sheet are sheets 9a to 9e hereinafter described.

Figures 1, 2A:
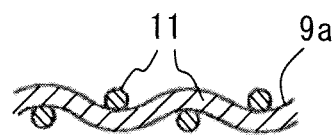

The sheet 9a has a cross section illustrated in FIG. 2A-1 in side view. A fiber 11 made of a plastic or metallic material and having a given wire diameter d is woven with a given aperture D in a plane weave pattern illustrated in FIG. 2A-2 in planar view, so that the sheet 9a has a large number of minute through holes 9a1. The sheet 9b has a cross section illustrated in FIG. 2B-1 in side view. The fiber is woven in a twill weave pattern illustrated in FIGS. 2B-2 in planar view, so that the sheet 9b has a large number of minute through holes 9b1.

Figure 3A:
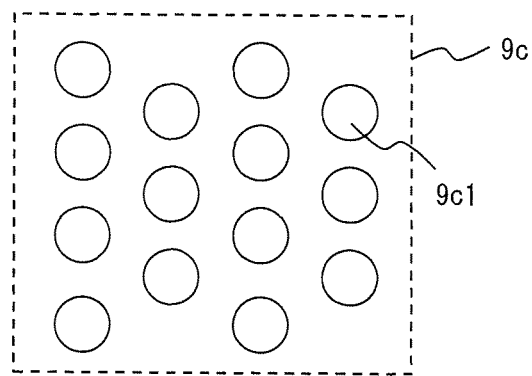
FIG. 3A is an enlarged planar view of a main part illustrating a third shape example (round holes) of the nano-sized particle classifying sheet provided in the inertial filter according to the preferred embodiment.
Figure 3B:
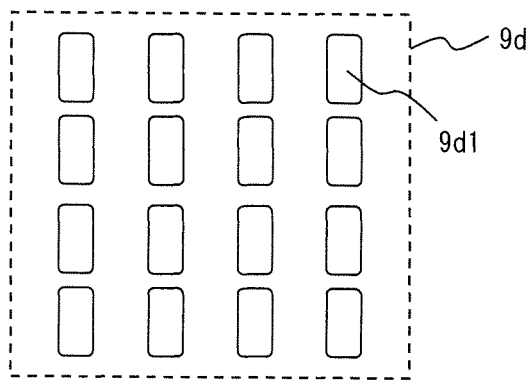
FIG. 3B an enlarged planar view of a main part illustrating a fourth shape example (oblong holes) of the nano-sized particle classifying sheet provided in the inertial filter according to the preferred embodiment.
Figure 3C:
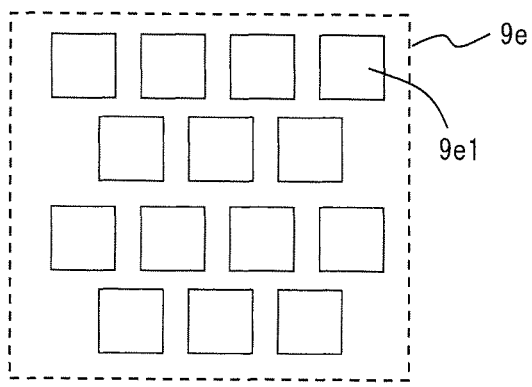
FIG. 3C an enlarged planar view of a main part illustrating a fifth shape example (square holes) of the nano-sized particle classifying sheet provided in the inertial filter according to the preferred embodiment.

The sheet 9c is obtained by forming a large number of minute through holes 9c1 in a circular shape by etching a conventional sheet. The sheet 9d has a large number of minute through holes 9d1 formed in an oblong shape as illustrated in FIG. 3B. The sheet 9e has a large number of minute through holes 9e1 formed in a square shape as illustrated in FIG. 3C.

Figures 4A, 4B:
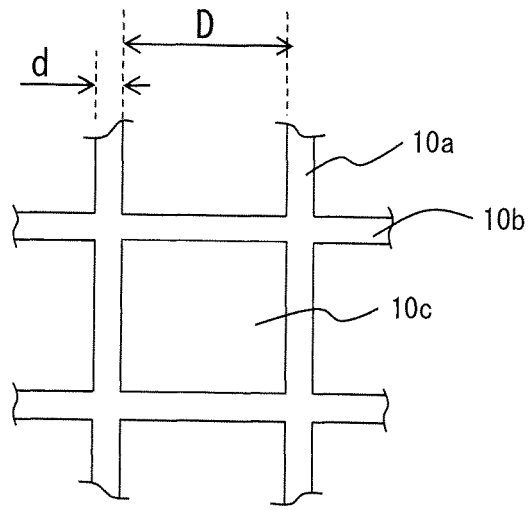
FIG. 4A an enlarged planar view of a main part illustrating shapes of nano-sized particle classifying sheets provided in a diffusion filter and the inertial filter.
FIG. 4B is a tabulated illustration for comparison of the shapes of the nano-sized particle classifying sheets provided in the diffusion filter and the inertial filter.

These through holes all have diameters required for classification of nano-sized particles. A description is given referring to FIGS. 4A and 4B. FIG. 4A shows through holes 10c formed in a mesh-like pattern by intersecting wires 10a and 10b with each other. Describing mesh-like shapes of diffusion and inertial filters, the diameter d of the wire 10a, 10b=about 20 μm, an aperture D representing the size of the through hole 10c=about 20 μm, and a fluid filtering speed is 0.001 to 0.1 m/s in the diffusion filter, whereas the diameter d=about 5 to 20 μm, the aperture D=about 40 to 300 μm, and the fluid filtering speed is 1 to 100 m/s in the inertial filter. The aperture is a largest diameter of a spherical particle that can pass through, and it is an aperture uniformity that plays an important role in achieving a good accuracy of classification. The aperture preferably stays in the foregoing numeral ranges to accomplish a better filtering intensity, less pressure loss, and a larger quantity of fluid flow.

Examples of the mesh-like particle classifying sheet in which plastic fibers are woven are; nylon mesh, polyester mesh, polypropylene mesh, Teflon (registered trademark) mesh, and polyethylene mesh. Other examples are fibers in which at least two different fibers are woven such as nylon mesh woven with a carbon fiber. The metal-fiber sheet is, for example, a mesh-like filter woven with SUS and others, or a metallic film having a large number of minute through holes formed therein by etching.

Thus, the mesh-like shape is a shape where plural minute through holes for classification are formed in a given area dimension, per unit length, or in a regular pattern. According to the present preferred embodiment, the particle classifying sheet 9 has a sheet area larger than the inner diameter of the downstream-side opening of the diametrically-reduced through aperture 5d, and the part 9a of the sheet is provided at the downstream-side opening of the diametrically-reduced through cavity 5d for classification of nano-sized particles. Such a simplified structure reduces the likelihood that the following unfavorable events possibly occur near an outer peripheral portion of the particle classifying sheet 9, adversely affect an accuracy of classification in the part 9a; minute through holes randomly arranged by the unraveled meshes, and any gaps between the outer peripheral portion of the particle classifying sheet 9 and the cylindrical plate 5b.

Because the diametrically-reduced through cavity 3b of the inertial filter 3 for removal of coarse particles is diametrically smaller toward the downstream side in the fluid passage direction, the velocity of fluid flow of the fluid passing therethrough is accelerated. The fluid then passes through the diametrically-constant through cavity 3c at a constant velocity, collecting any coarse particles therein. The diametrically-constant through cavity 3c has a filtering structure where the metal fiber 3d is stacked in layers, to which stokes number Stk and Peclet number Pe usable for selecting a velocity of gas flow and a fiber diameter are applicable. The Stokes number Stk is a dimensionless number representing tracking of particles relative to gas flow in filters made of metal fibers, the formula of which is omitted in this description. The Stokes number Stk is in proportion to a velocity of fluid flow, a particle density, and the square of a particle diameter but is in reverse proportion to a fiber diameter.

It is known from the formula of the Stokes number Stk that floating particles, starting from particles having larger particle diameters, fail to follow the gas flow as the velocity of gas flow increases, departing from a gas flow path and colliding with the metal fiber. By controlling the velocity of gas flow and selecting the fiber diameter referring to the Stokes number Stk, diameters of particles to be collected can be selected. The diameter of the metal fiber according to the present preferred embodiment is very small, which makes it unnecessary to increase the velocity of fluid flow to as high as an impactor. The metal fiber can collect particles not only by particle inertia but also by other mechanisms of collection leveraging blocking, gravity, static electricity, or diffusion.

The Peclet number Pe is a number representing a ratio of an effect of particle delivery by gas flow and an effect of particle delivery by diffusion, which is in proportion to the velocity of fluid flow and wire diameter but in reverse proportion to a diffusion coefficient. To lessen any influences from diffusion, it is necessary to increase the Peclet number Pe. As particle diameters are smaller, the diffusion coefficient is larger. Because a small value is selected as the fiber diameter, the velocity of fluid flow is preferably higher to improve the selectivity of particle diameters. Based on the description given so far, when the flow of velocity and the fiber diameter are arbitrarily selected (more specifically, at least one of the fiber diameter, aperture, porosity, and pore shapes in the particle classifying sheet is arbitrarily selected), targeted particles can be collected and classified by the metal fiber.

According to the present preferred embodiment, the quantity of the metal fiber 3d filling the diametrically-constant through cavity 3c of the inertial filter 3 for removal of coarse particles is changed to allow for adjustment of an internal porosity of the diametrically-constant through cavity 3c of the inertial filter 3 for removal of coarse particles, and the wire diameter of the metal fiber 3d is changed so as to minimize any pressure loss without largely undermining the flowability of gas flow in the diametrically-constant through cavity 3c. As a result, an effect of particle inertia necessary for removal of coarse particles can be obtained even when a small flow quantity is suctioned by a small gas flow suctioning pump.

The particle classifying sheet 9 of the inertial filter 5 for classification of nano-sized particles according to the present preferred embodiment can classify nano-sized particles. The particle classifying sheet 9 formed in the mesh-like shape is not compressed in the fluid passage direction under an action of fluid pressure, and the mesh-like shape can equalize the porosity and pore shapes. These advantages sharpen the effectiveness of classification. Because of the uniform filling rate of the particle classifying sheet 9, a classification diameter is easily controllable. The classification diameter is easily adjustable on site when, for example, the particle classifying sheet 9 is stacked in a large number of layers.

The fluid flowability in the particle classifying sheet 9 is hardly undermined. When a small quantity is suctioned by a small suctioning pump, therefore, an effect of particle inertia necessary for classification of nano-sized particles can be obtained with any pressure loss being minimized.

Figure 5:
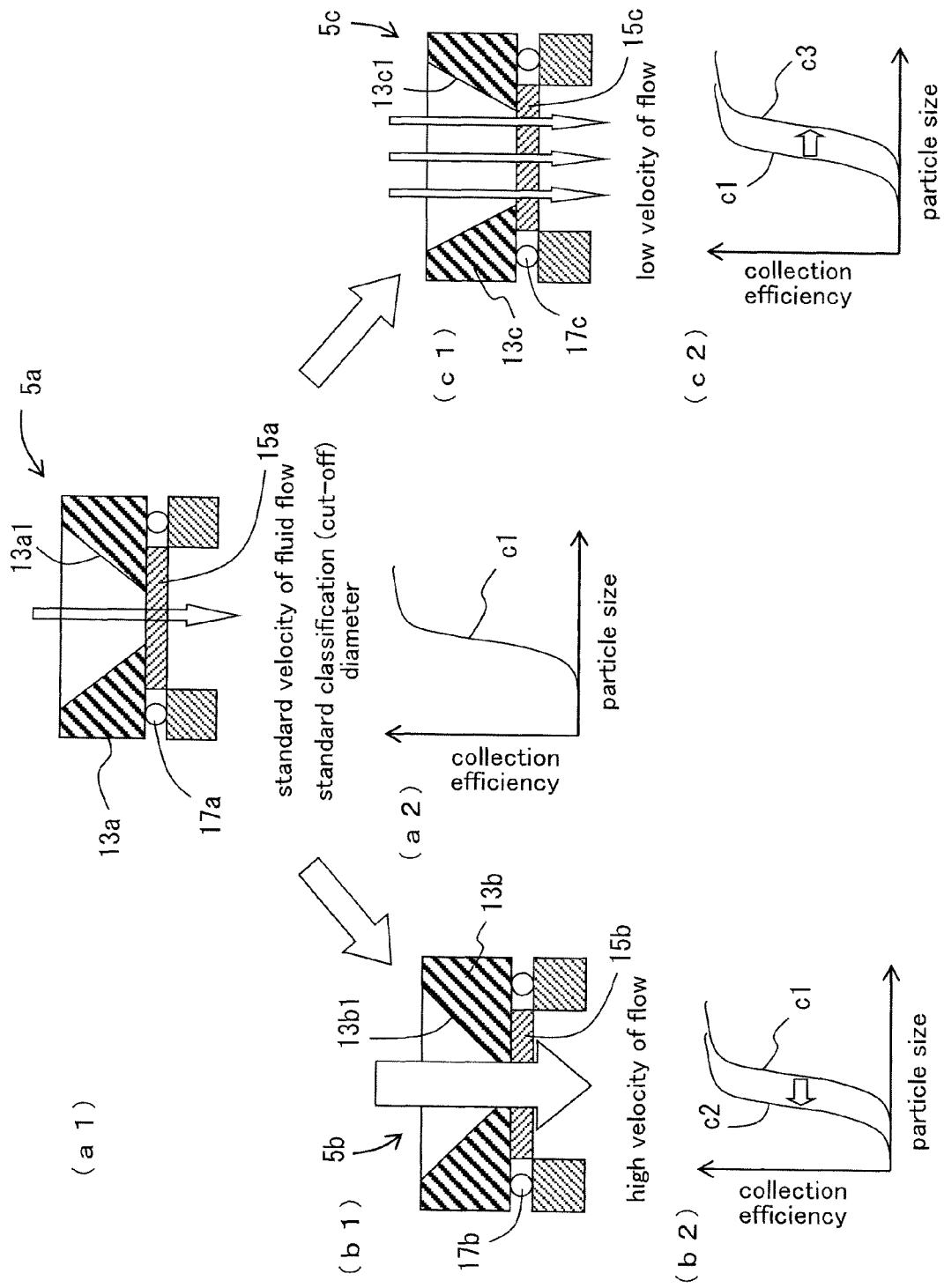
FIG. 5 are illustrations used to describe adjustment of a velocity of fluid flow by using a flow quantity adjusting nozzle of an inertial filter for classification of nano-sized particles used in the particle classification apparatus of FIG. 1.

The cylindrical plate 5b of the inertial filter 5 for classification of nano-sized particles illustrated in FIG. 1 is replaceable with flow quantity adjusting nozzles 13a to 13c as illustrated in FIGS. 5a1), b1), and c1) to allow for adjustment of the quantity of flow. On lower-end opening sides of the flow quantity adjusting nozzle 13a to 13c are provided particle classifying sheets 15a to 15c, and O rings 17a to 17c are fitted in outer peripheries of the particle classifying sheets 15a to 15c so that respective fluid flow paths illustrated with arrows in the drawings are sealed from outside.

Figures 2, 2A:
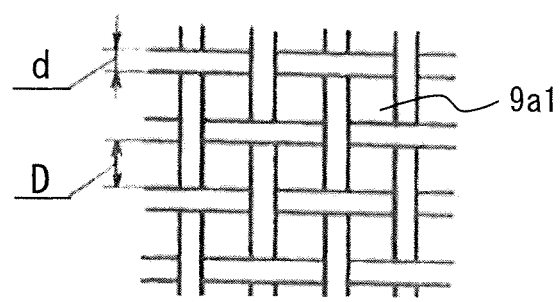
Figures 1, 2B:
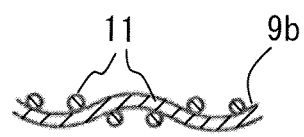
Figures 2, 2B:
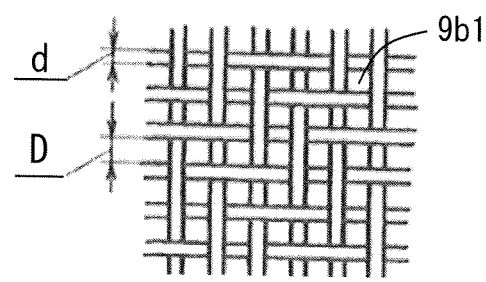

In the inertial filter 5a equipped with the flow quantity adjusting nozzle 13a illustrated in FIG. 5a1), a diametrically-reduced through cavity 13a1 is diametrically reduced by a conventional diameter reducing ratio per unit length in the fluid passage direction, and the fluid flows therethrough at a standard velocity of fluid flow. In FIG. 5a2), where a lateral axis represents a particle diameter and a vertical axis represents a collection efficiency, collecting characteristics result in characteristics c1. In the inertial filter 5b equipped with the flow quantity adjusting nozzle 13b illustrated in FIG. 5b1), a diametrically-reduced through cavity 13b1 of the flow quantity adjusting nozzle 13b is diametrically reduced by a large diameter reducing ratio, and the velocity of fluid flow is thereby increased. Therefore, the collecting characteristics shift from the characteristics c1 to characteristics c2 as illustrated in FIG. 5b2), resulting in a smaller 50% cut-off (classification) diameter. In the inertial filter 5c equipped with the flow quantity adjusting nozzle 13c illustrated in FIG. 5c1), a diametrically-reduced through cavity 13c1 of the flow quantity adjusting nozzle 13c is diametrically reduced by a small diameter reducing ratio, and the velocity of fluid flow is reduced. Therefore, the collecting characteristics shift from the characteristics c1 to characteristics c3 as illustrated in FIG. 5c2), increasing the classification diameter.

In the case of a constant quantity of flow, the flow quantity adjusting nozzle is replaced with the flow quantity adjusting nozzles 13a to 13c to change the classification diameter through stages, so that a particle distribution is obtained. When these nozzles are connected to, for example, any apparatus having a different quantity of fluid flow, the classification diameter is fixed as far as the velocity of fluid flow is set to a constant velocity. This is particularly advantageous for specific fields of application where the classification diameter should be fixed, such as environmental measurements.

Figures 1, 6A:
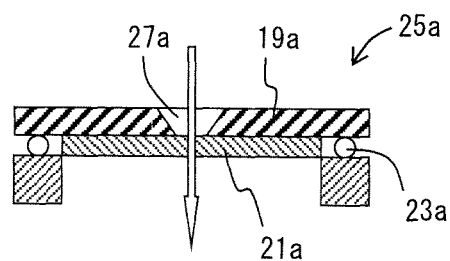
Figures 2, 6A:
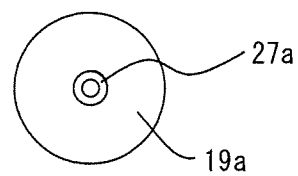
Figures 3, 6A:
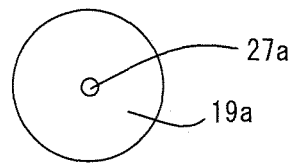
Figures 1, 6B:
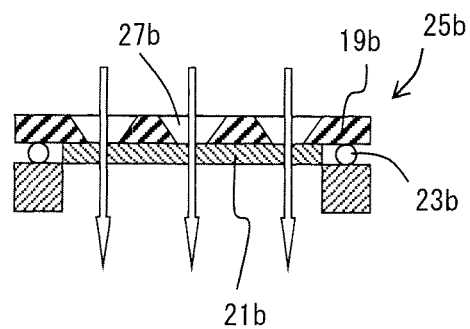
Figures 2, 6B:
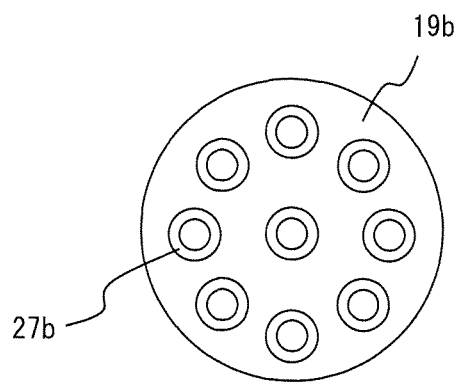
Figures 3, 6B:
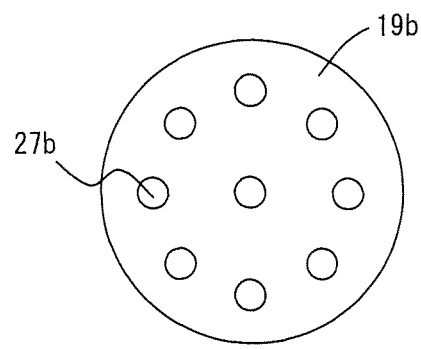

The flow quantity adjustment by the flow quantity adjusting nozzle is described referring to FIGS. 6A-1 to 6A-3. An inertial filter 25a illustrated in FIG. 6A-1 has a flow quantity adjusting nozzle 19a, a particle classifying sheet 21a, and an O ring 23a. FIG. 6A-2 is a top view of the flow quantity adjusting nozzle 19a, while FIG. 6A-3 is a back view of the flow quantity adjusting nozzle 19a. An inertial filter 25b illustrated in FIG. 6B-1 has a flow quantity adjusting nozzle 19b, a particle classifying sheet 21b, and an O ring 23b. FIG. 6B-2 is a top view of the flow quantity adjusting nozzle 19b, while FIG. 6B-3 is a back view of the flow quantity adjusting nozzle 19b. The arrows illustrated in the drawings denote the fluid passage direction.

In the inertial filter 25a illustrated in FIG. 6A-1, the flow quantity adjusting nozzle 19a has a diametrically-reduced through cavity 27a. In contrast, the flow quantity adjusting nozzle 19b of the inertial filter 25b illustrated in FIG. 6B-1 has a plurality of diametrically-reduced through cavities 27b, wherein the classifying characteristics are stabilized, and the quantity of fluid flow can be increased.

Figure 7:
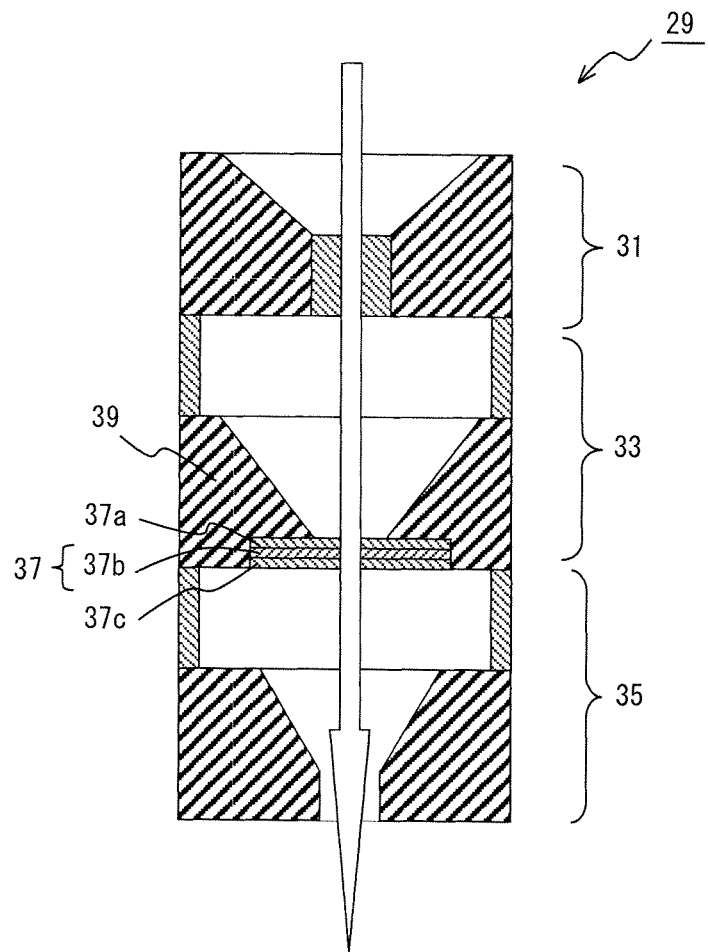
FIG. 7 is a side view of a particle classification apparatus wherein the inertial filter according to the preferred embodiment is provided in a plural number.
Figure 8:
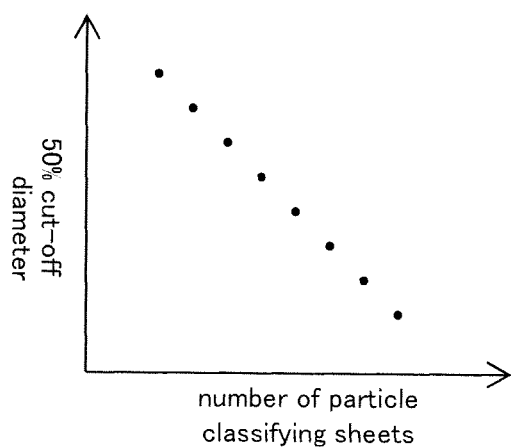
FIG. 8 is a graphical illustration of 50% cut-off diameters for different numbers of particle classifying sheets.

A particle classification apparatus according to another embodiment of the invention is described referring to FIG. 7. Similarly to the illustration of FIG. 1, a particle classification apparatus 29 includes an inertial filter 31 for removal of coarse particles, an inertial filter 33 for classification of nano-sized particles, and a particle collector/apparatus introduction unit 35. The apparatus further includes a particle classifying sheet 37 provided in the inertial filter 33 for classification of nano-sized particles, wherein a plurality of particle classifying sheets 37a to 37c constitute the particle classifying sheet 37. In such a multilayered structure where the particle classifying sheets 37a to 37c are stacked in layers, the classification diameter is smaller as the number of layers is larger as illustrated in classifying characteristics of FIG. 8, where a lateral axis represents the number of the layered particle classifying sheets and a vertical axis represents the 50% cut-off diameter (classification diameter). This structure is advantageous for adjustment of the classification diameter on site. A reference numeral 39 is a flow quantity adjusting nozzle of the inertial filter 33 for classification of nano-sized particles. The particle classifying sheet 37 illustrated in FIG. 7 includes three sheets for illustrative convenience, however, the number of the sheets is not necessarily limited to three.

Figure 9A:
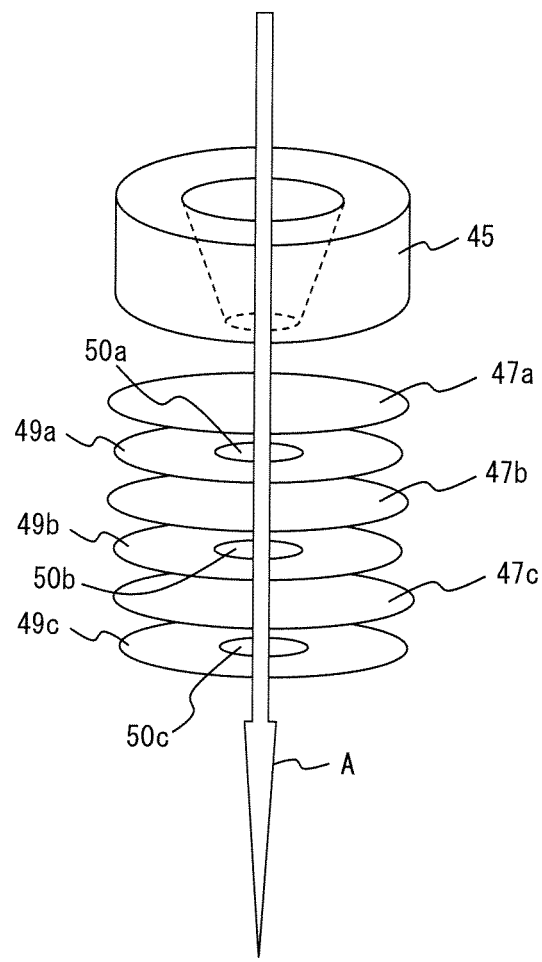
FIG. 9A is a perspective view of an external structure wherein the inertial filters for classification of nano-sized particles illustrated in FIG. 7 are disassembled.
Figure 9B:
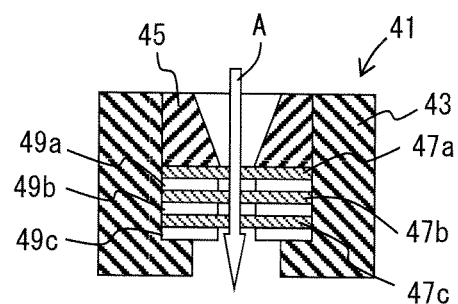
FIG. 9B is a perspective view of an external structure wherein the inertial filters for classification of nano-sized particles illustrated in FIG. 7 are assembled FIG. 10 are illustrations used to describe a particle size—collection efficiency relationship when number of particle classifying sheets is changed in the particle classification apparatus where the inertial filter of FIG. 7 is used.

FIG. 9A illustrates an inertial filter 41 for classification of nano-sized particles, and FIG. 9B is an exploded view of the filter. The inertial filter 41 for classification of nano-sized particles includes a replaceable flow quantity adjusting nozzle 45 in a filter case 43, and a plurality of replaceable particle classifying sheets 47a to 47c and a plurality of replaceable intermediary spacers 49a to 49c.

The particle classifying sheets 47a to 47c each has a given sheet thickness dimension and a circular sheet area larger than a circular area dimension of a downstream-side opening of the flow quantity adjusting nozzle 45. These sheets are partly facing the downstream-side opening of the flow quantity adjusting nozzle 4. The intermediary spacers 49a to 49c are stacked in layers alternating with the particle classifying sheets 47a to 47c and have a circular shape and an area dimension equal to those of the particle classifying sheets 47a to 47c. The intermediary spacers 49a to 49c have an equal spacer thickness dimension and have through holes 50a to 50c diametrically equal to the downstream-side opening of the flow quantity adjusting nozzle 45. The through holes 50a to 50c combined by the layered structure of the intermediary spacers 49a to 49c form a through hole where the velocity of fluid flow becomes constant.

According to the inertial filter 41 for classification of nano-sized particles illustrated in FIGS. 9A and 9B, the parts constituting the filter are replaceable and differently combined. The different combinations of these parts facilitate control of the velocity of fluid flow and particle classification.

Figure 10:
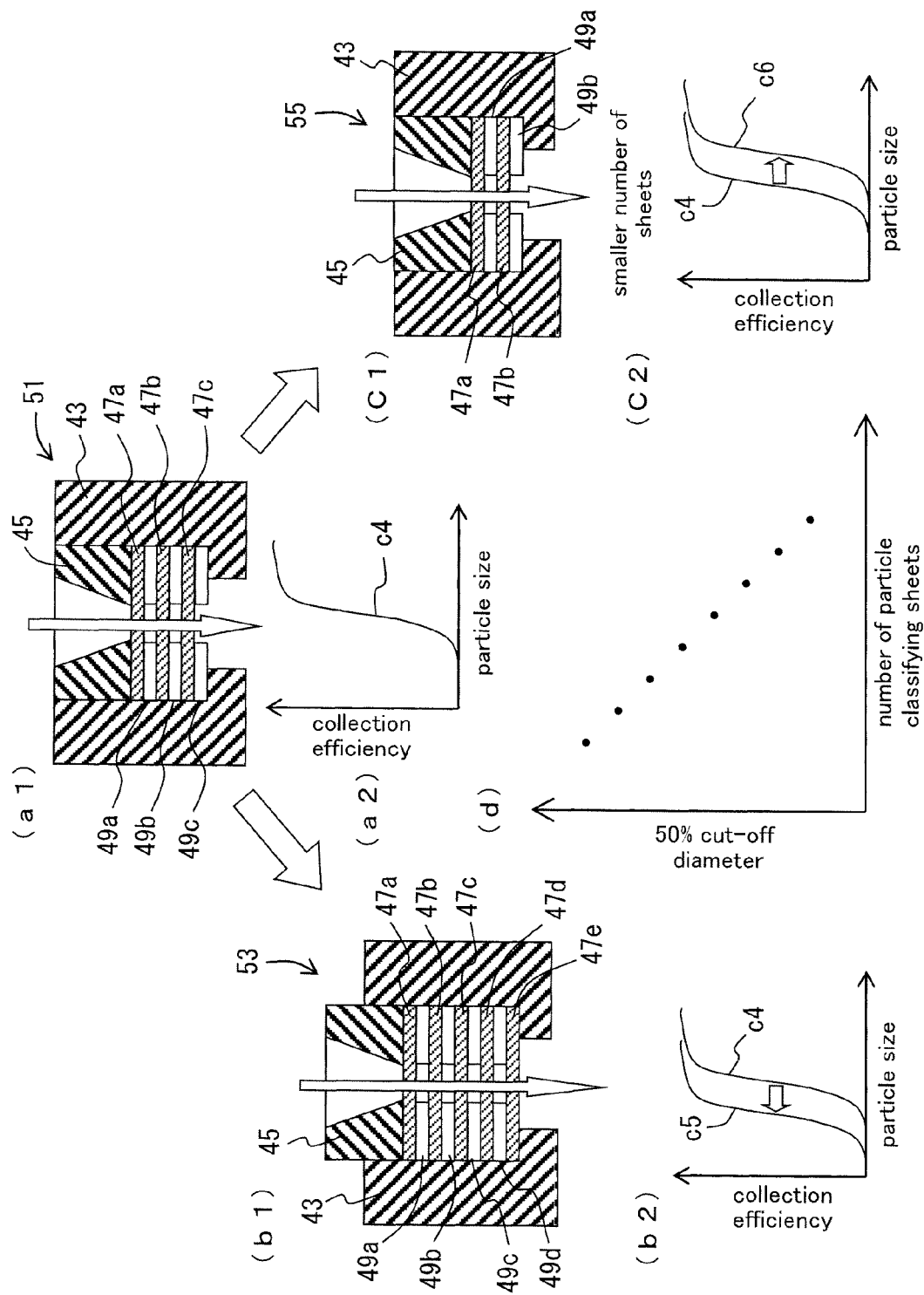

Referring to FIG. 10 are described examples in which the particle classifying sheets 47a to 47c and the replaceable intermediary spacers 49a to 49c are differently combined in the inertial filter 41 for classification of nano-sized particles illustrated in FIGS. 9A and 9B to control the classification diameter. FIG. 10a1) illustrates an inertial filter 51 having three particle classifying sheets 47a to 47c and three intermediary spacers 49a to 49c. FIG. 10a2) illustrates classifying characteristics c4 of the filter. FIG. 10b1) illustrates an inertial filter 53 having five particle classifying sheets 47a to 47e and four intermediary spacers 49a to 49d. FIG. 10b2) illustrates classifying characteristics c5 of the filter. FIG. 10c1) illustrates an inertial filter 55 having two particle classifying sheets 47a and 47b and two intermediary spacers 49a and 49b. FIG. 10c2) illustrates classifying characteristics c6 of the filter. FIG. 10d) illustrates classification diameter characteristics, where a lateral axis represents the number of particle classifying sheets and a vertical axis represents the classification diameter. It is known from the illustration of FIG. 10d)

that the classification diameter is smaller as the number of the particle classifying sheets is larger.

Figure 11:
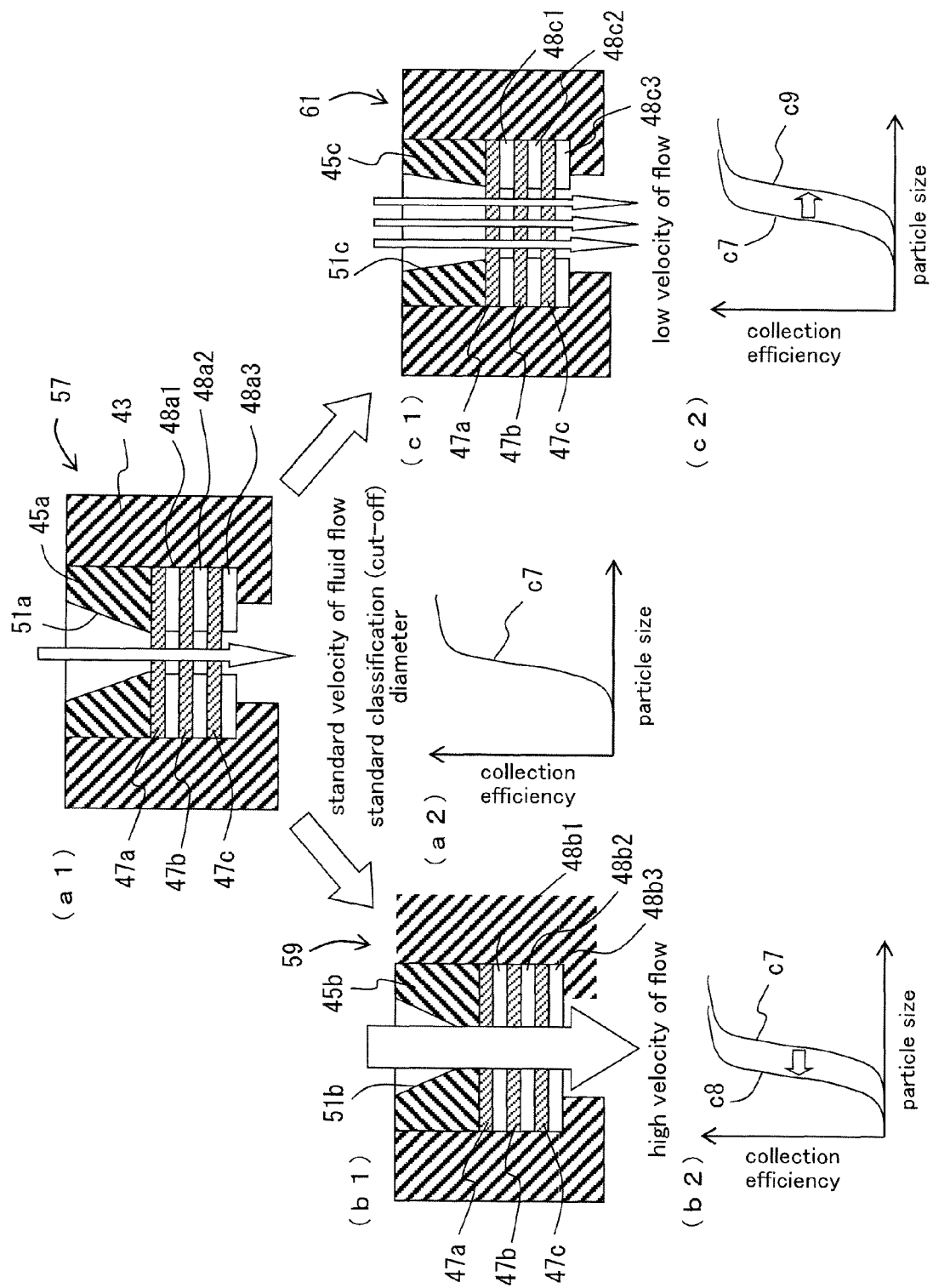
FIG. 11 are illustrations used to describe a particle size—collection efficiency relationship when a flow quantity adjusting nozzle and a plurality of intermediary spacers are differently combined in the particle classification apparatus where the inertial filter of FIG. 7 is used.

Referring to FIG. 11 are described examples in which the classification diameter is controlled by a flow quantity adjusting nozzle and intermediary spacers. FIG. 11a1) illustrates an inertial filter 57 having a flow quantity adjusting nozzle 45a which applies a standard velocity of fluid flow, particle classifying sheets 47a to 47c, and intermediary spacers 48a1 to 48a3. FIG. 11a2) illustrates classifying characteristics c7 of the inertial filter 57. The classifying characteristics c7 are accomplished by a diameter reducing ratio of a diametrically-reduced through cavity 51a of the flow quantity adjusting nozzle 45a per unit length in the fluid passage direction and the intermediary spacers 48a1 to 48a3. This is used as a standard velocity of fluid flow. FIG. 11b1) illustrates an inertial filter 59 having a flow quantity adjusting nozzle 45b which applies a velocity of fluid flow higher than the standard velocity of fluid flow, particle classifying sheets 47a to 47c, and intermediary spacers 48b1 to 48b3. FIG. 11b2) illustrates classifying characteristics c8 of the inertial filter 59.

A diametrically-reduced through cavity 51b of the flow quantity adjusting nozzle 45b has a large diameter reducing ratio, and the intermediary spacers 48b1 to 48b3 have small through holes. Therefore, the velocity of fluid flow is higher than the standard velocity of fluid flow, resulting in a larger effect of inertial impaction of nano-sized particles in the fluid. Then, the classifying characteristics shift from the characteristics c7 to the characteristics c8, enabling to collect nano-sized particles having smaller particle sizes.

FIG. 11c1) illustrates an inertial filter 61 having a flow quantity adjusting nozzle 45c which applies a velocity of fluid flow higher than the standard velocity of fluid flow, particle classifying sheets 47a to 47c, and intermediary spacers 48c1 to 48c3. FIG. 11c2) illustrates classifying characteristics c9 of the inertial filter 61.

A diametrically-reduced through cavity 51c of the flow quantity adjusting nozzle 45b has a small diameter reducing ratio, and the intermediary spacers 48c1 to 48c3 have large through holes. Therefore, the velocity of fluid flow is lower than the standard velocity of fluid flow, resulting in a smaller effect of inertial impaction of nano-sized particles in the fluid. As a result, the classifying characteristics shift from the characteristics c7 to the characteristics c9.

As is clear from these drawings, the classification diameter can be controlled by differently combining the flow quantity adjusting nozzles 45a to 45c, and intermediary spacers 48a1 to 48a3, 48b1 to 48b3, and 48c1 to 48c3.

Figure 12:
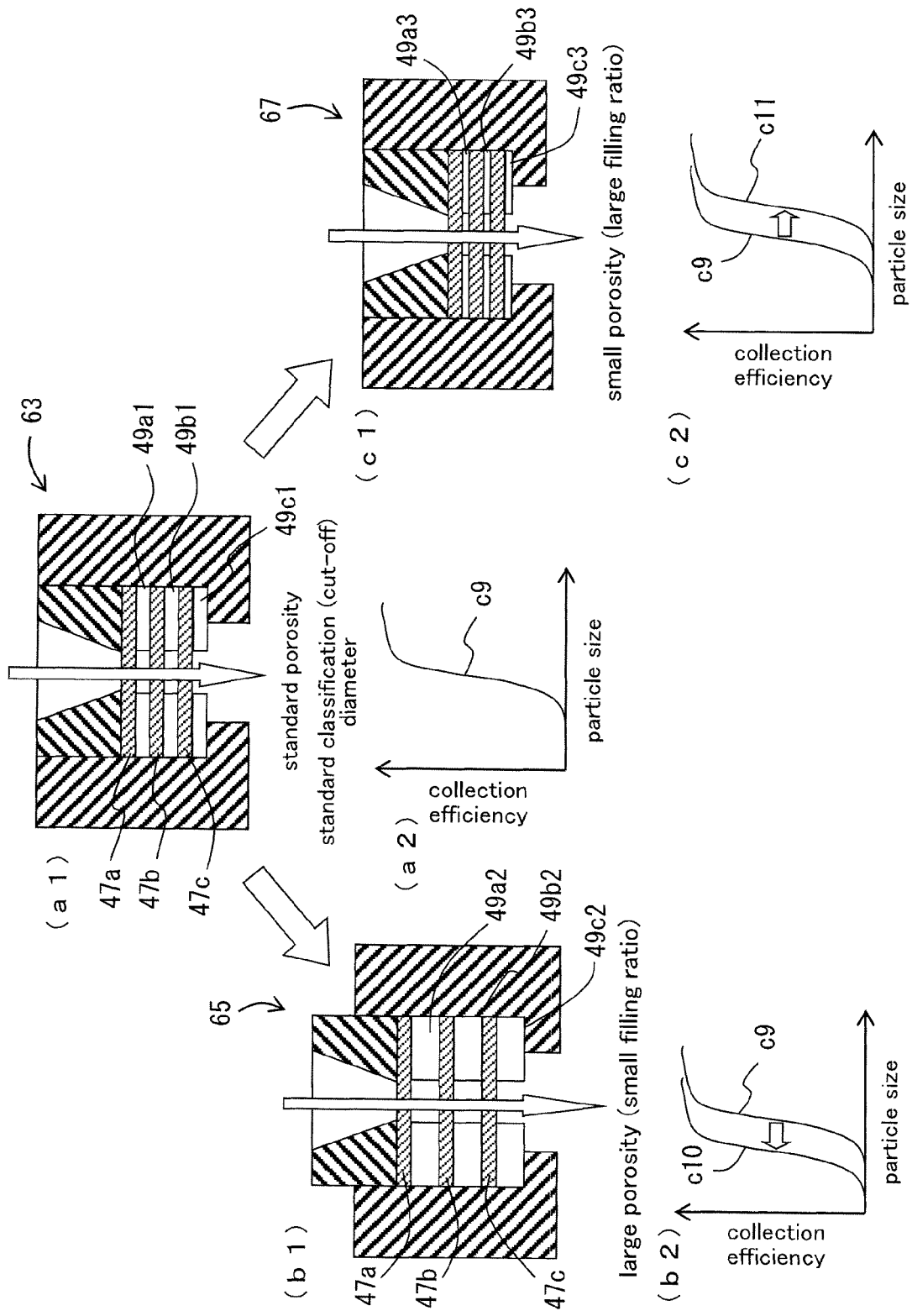
FIG. 12 are illustrations used to describe a particle size—collection efficiency relationship when plural inertial filters are spaced at different intervals in the particle classification apparatus where the inertial filter of FIG. 7 is used.

Referring to FIG. 12 are described examples in which the particle diameter is controlled by intermediary spacers. FIG. 12a1) illustrates an inertial filter 63 having intermediary spacers 49a1 to 49c1 which apply a standard porosity. FIG. 12a2) illustrates classifying characteristics c9 of the inertial filter 63. The porosity of the inertial filter 63 is used as a standard porosity, spacer thicknesses of the intermediary spacers 49a1 to 49c1 in the inertial filter 63 are respectively t, and a diametrically-constant through passage formed by the intermediary spacers 49a1 to 49c1 has a length of 3 t in total. Reference numerals 47a to 47c are particle classifying sheets.

FIG. 12b1) illustrates an inertial filter 65 having intermediary spacers 49a2 to 49c2. FIG. 12b2) illustrates classifying characteristics c10 of the inertial filter 65. In the inertial filter 65, spacer thicknesses of the intermediary spacers 49a2 to 49c2 are respectively, for example, 2 t, and a diametrically-constant through passage formed by the intermediary spacers 49a2 to 49c2 has a length of 6 t in total. This increases the porosity (filling ratio is smaller), enabling to collect nano-sized particles having smaller particle sizes.

FIG. 12c1) illustrates an inertial filter 67 having intermediary spacers 49a3 to 49c3. FIG. 12c2) illustrates classifying characteristics c11 of the inertial filter 67. In the inertial filter 67, spacer thicknesses of the intermediary spacers 49a3 to 49c3 are respectively, for example, 0.5 t, and a diametrically-constant through passage formed by the intermediary spacers 49a3 to 49c3 has a length of 1.5 t in total as compared to the inertial filter 63. This decreases the porosity (filling ratio is larger). As is clear from these drawings, the classification diameter is controllable as illustrated in FIGS. 12a2), b2), and c2) by differently combining the intermediary spacers.

Figures 1, 13A:
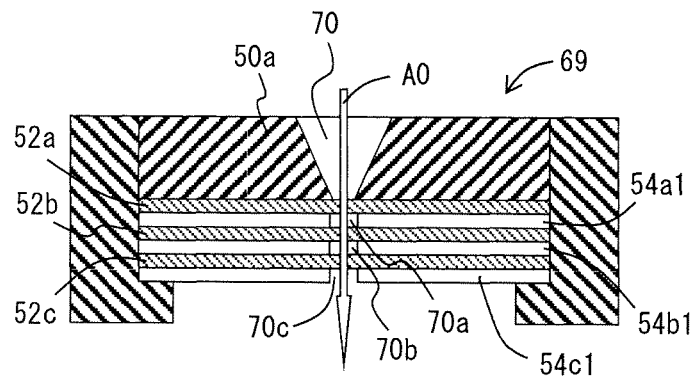
Figures 2, 13A:
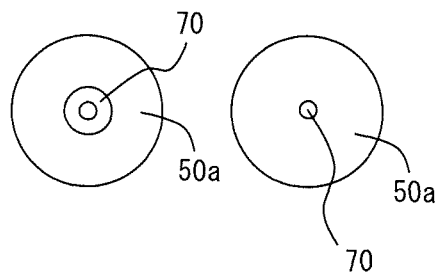
Figures 3, 13A:
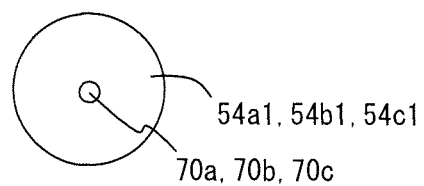

Referring to FIGS. 13A-1 to 13B-3 is described an example in which the quantity of fluid flow is adjusted by a flow quantity adjusting nozzle and intermediary spacers. An inertial filter 69 illustrated in FIG. 13A-1 has a flow quantity adjusting nozzle 50a, particle classifying sheets 52a to 52c, and intermediary spacers 54a1 to 54c1. FIG. 13A-2 illustrates a top view and a back view of the flow quantity adjusting nozzle 50a, and FIG. 13A-3 illustrates a top view of the intermediary spacers 54a1 to 54c1. The flow quantity adjusting nozzle 50a, particle classifying sheets 52a to 52c, and intermediary spacers 54a1 to 54c1 have an equal outer dimension in a plane orthogonal to the fluid passage direction. The particle classifying sheets 52a to 52c are stacked in layers being alternately interposed between the flow quantity adjusting nozzle 50a and the intermediary spacers 54a1 to 54c1. The intermediary spacers 54a1 to 54c1 each has a through hole, and these through holes 70a to 70c are diametrically equal to a downstream-side opening of a diametrically-reduced through cavity 70 of the flow quantity adjusting nozzle 50a. The through holes 70a to 70c overlap with one another at a position in a fluid passage direction A0.

Figures 1, 13B:
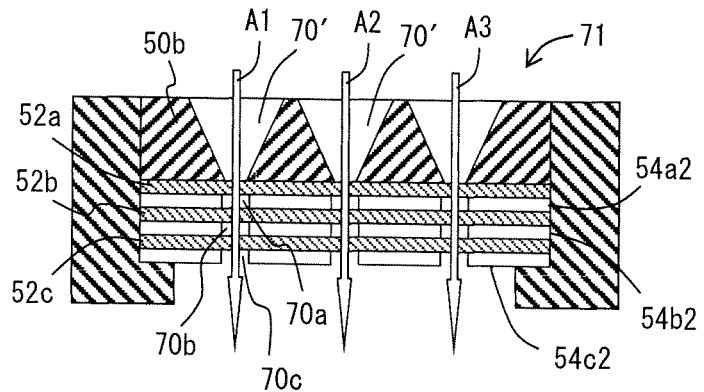
Figures 2, 13B:
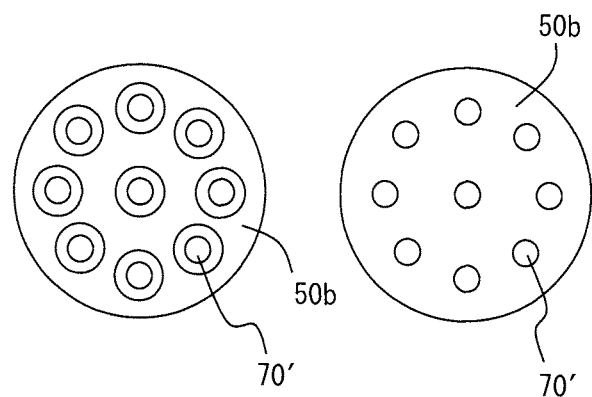
Figures 3, 13B:
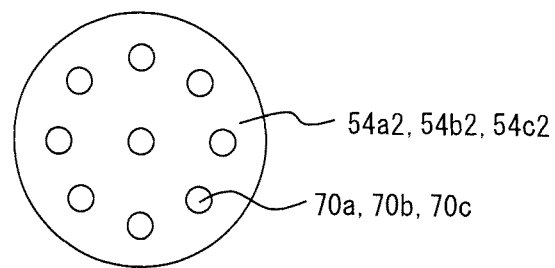

An inertial filter 71 illustrated in FIG. 13B-1 has a flow quantity adjusting nozzle 50b, particle classifying sheets 52a to 52c, and intermediary spacers 54a2 to 54c2. FIG. 13B-2 illustrates a top view and a back view of the flow quantity adjusting nozzle 50b, and FIG. 13B-3 illustrates a top view of the intermediary spacers 54a2 to 54c2. The flow quantity adjusting nozzle 5b, particle classifying sheets 52a to 52c, and intermediary spacers 54a2 to 54c2 have an equal outer dimension in a plane orthogonal to the fluid passage direction. The particle classifying sheets 52a to 52c are stacked in layers being alternately interposed between the flow quantity adjusting nozzle 50b and the intermediary spacers 54a2 to 54c2. The flow quantity adjusting nozzle 50b has a plurality of the diametrically-reduced through cavities 70 formed therein. The intermediary spacers 54a2 to 54c2 have a plurality of through holes 70a to 70c corresponding to and diametrically equal to downstream-side openings of a plurality of through cavities 70' of the flow quantity adjusting nozzle 50b. The plurality of through holes 70a to 70c overlap with one another at a position in each of fluid passage directions A1 to A3.

The inertial filter 69 illustrated in FIG. 13A-1 and the inertial filter 71 illustrated in FIG. 13B-1 respectively have different numbers of through passages in the fluid passage direction. However, the velocity of fluid flow of the inertial filter 69 illustrated in FIG. 13A-1 in the fluid passage direction A0 and the velocity of fluid flow of the inertial filter 71 illustrated in FIG. 13B-1 in the fluid passage directions A1 to A3 can be arranged to be constant and equal, or the inertial filter 69 can be arranged to have a larger quantity of flow than the inertial filter 71.

A practical use of the inertial filter according to the present preferred embodiment is described referring to FIG. 14. FIG. 14 illustrates classifying characteristics of the inertial filter, where a lateral axis represents an aerodynamic diameter and a vertical axis represents a collection efficiency. A reference symbol c12 is classifying characteristics based on theoretical values. In the drawing, black squares ♦ and black triangles ▲ show classifying characteristics of first and second inertial filters having five particle classifying sheets and five intermediary spacers, and x shows classifying characteristics of a third inertial filter having five particle classifying sheets and 20 intermediary spacers. ΔP=4.14, 4.34, 5.41 (kPa), which are respectively initial pressure losses of the first to third inertial filters, and cut-off diameter=165, 160, 130 (nm), which are respectively classification diameters of the first to third inertial filters. In these filters, a quantity of fluid flow is 1.5 liter/min. Thus, the inertial filter according to the present preferred embodiment has favorable classifying characteristics where theoretical values and experimental value are substantially equal.

Figure 15:
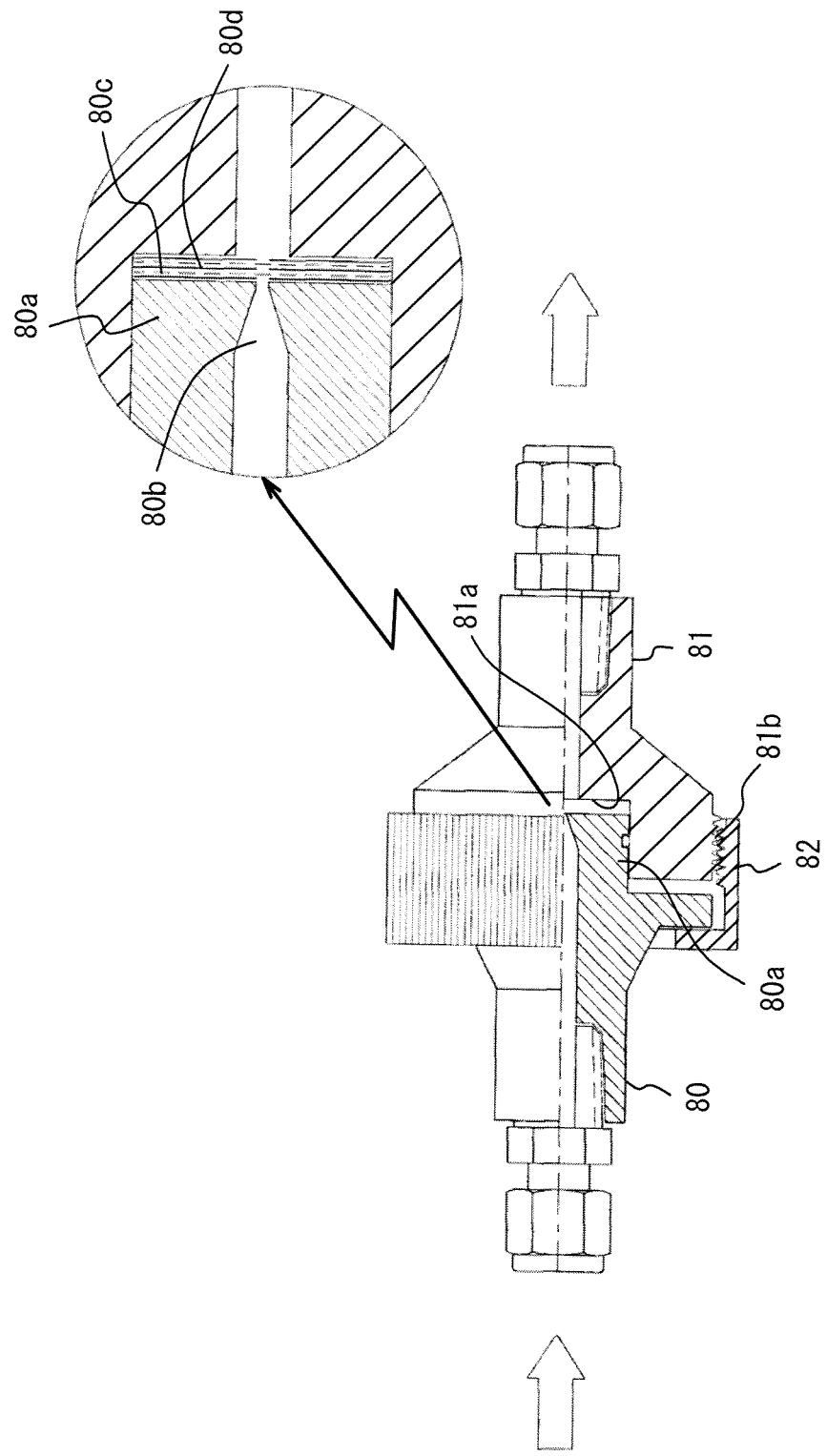
FIG. 15 is an illustration of the inertial filter according to the preferred embodiment.
Figure 16:
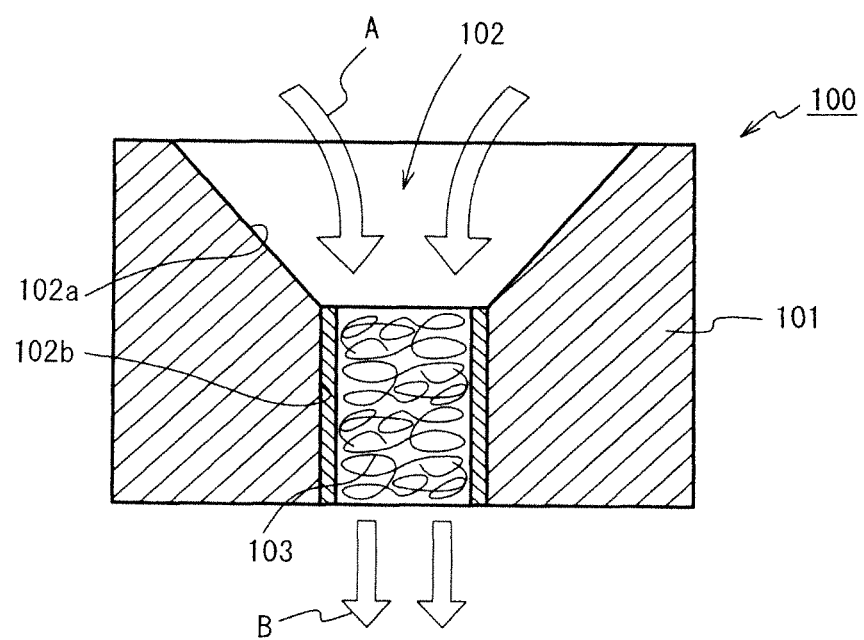
FIG. 16 is a side view of a conventional inertial filter.

FIG. 15 illustrates an inertial filter as a final product. The inertial filter includes a pair of cylindrical male and female connectors 80 and 81, wherein a protruding edge portion 80a of the male connector 80 is fitted in a dented portion 81a of the female connector 81 to form a fluid flow path in a direction illustrated with arrows. Then, a nut 82 is screwed into a spiral groove 81 on an outer periphery of the female connector 81 from the side of the male connector 80 so that the connectors 80 and 81 are fastened to each other with the nut 82. Then, a through cavity 80b diametrically smaller in the arrow direction, and a plurality of particle classifying sheets 80c and intermediary spacers 80d are provided in the protruding edge portion 80a of the male connector 80.

As described so far, the inertial filter according to the present preferred embodiment is equipped with a particle classifying sheet having a plurality of particle classifying holes uniformly arranged, wherein the particle classifying sheet has an area larger than a fluid passage area at a site where the sheet is placed, and a part of the sheet is provided in the form of a partition wall dividing a fluid flow path in two sections in a fluid passage direction. Therefore, aimed initial classifying characteristics are easily obtainable, and the classifying characteristics are stabilized over a long period of time unlike any conventional inertial filter having a diametrically-constant through cavity filled with fiber. Such a conventional inertial filter having a diametrically-constant through cavity filled with fiber had the problems; initial classifying characteristics are difficult to control because of the lack of uniformity in a filling density, orientation, and pore shapes of the fiber, and the stability of the classifying operation is undermined by compression of the fiber in the fluid passage direction under pressure applied from gas flow during the classifying operation. The inertial filter according to the present preferred embodiment can solve these technical problems. Further, the inertial filter according to the present preferred embodiment, wherein the sheet is used in place of the fiber, is more easily washable, which facilitates reuse of the inertial filter. Thus, the invention provides an advantageous inertial filter wherein aimed initial classifying characteristics are easily achievable, and a good collection efficiency is unlikely to deteriorate over a long period of time, enabling to reliably classify particles.

INDUSTRIAL APPLICABILITY

The invention is applicable to an inertial filter placed in a fluid flow path to classify particles of fluid by an effect of inertial impaction, and a particle classification apparatus equipped with the inertial filter.

DESCRIPTION OF REFERENCE SYMBOLS 1 particle classification apparatus
3 inertial filter for removal of coarse particles
5 inertial filter for classification of nano-sized particles
9 particle classifying sheet

The invention claimed is:

1. An inertial filter placed in a fluid flow path for passage of a fluid containing nano-sized particles to collect the nano-sized particles in the fluid flow path by an effect of particle inertia, the inertial filter collecting the nano-sized particles having smaller particle sizes as a velocity of flow of the fluid is increased, the inertial filter including:
   a flow quantity adjusting nozzle located on an upstream side of the fluid flow path and having a diametrically-reduced through cavity diametrically smaller in the fluid passage direction, the flow quantity adjusting nozzle adjusting the velocity of fluid flow depending on different forms of the diametrically-reduced through cavity; and
   a particle classifying sheet located further on a downstream side of the fluid flow path than the flow quantity adjusting nozzle and having a plurality of particle classifying holes uniformly arranged, the plurality of particle classifying holes being formed to collect the nano-sized particles by an effect of particle inertia, the particle classifying sheet having a sheet area larger than a downstream-side opening of the diametrically-reduced through cavity and being provided in the form of a partition wall dividing the fluid flow path in two sections in the fluid passage direction so as to block a whole area of the downstream-side opening, wherein
   the flow quantity adjusting nozzle is replaceable with another flow quantity adjusting nozzle having a different number of the diametrically-reduced through cavities to allow for adjustment of a quantity of flow of the fluid.

2. The inertial filter as claimed in claim 1, wherein a sheet constitutes the particle classifying sheet in the fluid passage direction.

3. The inertial filter as claimed in claim 1, wherein a plurality of laminated sheets constitutes the particle classifying sheet in the fluid passage direction.

4. The inertial filter as claimed in claim 1, wherein the particle classifying sheet is a sheet having plural minute through holes for classification formed regularly per a given area dimension or a constant length dimension.

5. The inertial filter as claimed in claim 4, wherein the particle classifying sheet is a sheet having a wire diameter ranging from 5 to 20 μm and an aperture ranging from 40 to 300 μm.

6. The inertial filter as claimed in claim 1, wherein the flow quantity adjusting nozzle is provided in a manner that the flow quantity adjusting nozzle is replaceable with another flow quantity adjusting nozzle having a diametrically-reduced through cavity diametrically reduced by a different diameter reducing ratio to allow for adjustment of the velocity of flow of the fluid.

7. The inertial filter as claimed in claim 1, wherein the particle classifying sheet is provided in a manner that the particle classifying sheet is replaceable with another particle classifying sheet in which at least one of a fiber diameter, an aperture, a porosity, and a pore shape is different.

8. The inertial filter as claimed in claim 1, wherein an intermediary spacer is interposed between a plurality of the particle classification sheets in the fluid passage direction, and the intermediary spacer is provided in a manner that the intermediary spacer is replaceable with another intermediary spacer having a through hole diametrically different.

9. The inertial filter as claimed in claim 1, wherein a plurality of the particle classifying sheets are stacked on each other with an intermediary spacer interposed therebetween.

10. The inertial filter as claimed in claim 9, wherein the particle classifying sheet is replaceable with another particle classifying sheet in which at least one of a fiber diameter, an aperture, a porosity, and a pore shape is different to allow for control of the particle classification.

11. The inertial filter as claimed in claim 10, wherein the particle classification is controllable by changing number of the particle classifying sheets stacked in layers.

12. The inertial filter as claimed in claim 9, wherein the particle classification is controllable by changing number of the intermediary spacers stacked in layers.

13. The inertial filter as claimed in claim 9, wherein the flow quantity adjusting nozzle is replaceable with another flow quantity adjusting nozzle having a different flow path to allow for adjustment of the velocity of flow of the fluid.

14. The inertial filter as claimed in claim 9, wherein the intermediary spacer is replaceable with another intermediary spacer having a through hole diametrically different to allow for adjustment of the velocity of flow of the fluid.

15. The inertial filter as claimed in claim 10, wherein the particle classification is controllable by changing a spacer thickness dimension of the intermediary spacer.

16. The inertial filter as claimed in claim 10, wherein number of the flow paths of the flow quantity adjusting nozzle and number of through holes of the intermediary spacer corresponding to the number of the flow paths are changed to allow for adjustment of the quantity of fluid flow.

17. A particle classification apparatus equipped with an inertial filter filled with an incompressible fiber on an upstream side in a fluid passage direction for removal of coarse particles and the inertial filter as claimed in claim 1 on a downstream side in the fluid passage direction for classification of nano-sized particles.

18. An inertial filter placed in a fluid flow path for passage of a fluid containing nano-sized particles to collect the nano-sized particles in the fluid flow path by an effect of particle inertia, the inertial filter collecting the nano-sized particles having smaller particle sizes as a velocity of flow of the fluid is increased, the inertial filter including:

a flow quantity adjusting nozzle located on an upstream side of the fluid flow path and having a diametrically-reduced through cavity diametrically smaller in the fluid passage direction, the flow quantity adjusting nozzle adjusting the velocity of fluid flow depending on different forms of the diametrically-reduced through cavity; and a particle classifying sheet located further on a downstream side of the fluid flow path than the flow quantity adjusting nozzle and having a plurality of particle classifying holes uniformly arranged, the plurality of particle classifying holes being formed to collect the nano-sized particles by an effect of particle inertia, the particle classifying sheet having a sheet area larger than a downstream-side opening of the diametrically-reduced through cavity and being provided in the form of a partition wall dividing the fluid flow path in two sections in the fluid passage direction so as to block a whole area of the downstream-side opening, wherein the flow quantity adjusting nozzle is replaceable with another flow quantity adjusting nozzle having a diametrically-reduced through cavity diametrically reduced by a different diameter reducing ratio to allow for adjustment of the velocity of fluid flow.

* * * * *